United States Patent [19]

Baker et al.

[11] Patent Number: 4,716,109
[45] Date of Patent: * Dec. 29, 1987

[54] IMMUNOASSAY

[75] Inventors: Terence S. Baker, Staines; Michael J. Powell; Richard C. Titmas, both of Maidenhead, all of England

[73] Assignee: Boots-Celltech Diagnostics Limited, Slough, England

[*] Notice: The portion of the term of this patent subsequent to May 6, 2003 has been disclaimed.

[21] Appl. No.: 575,390

[22] Filed: Jan. 30, 1984

[30] Foreign Application Priority Data

Jan. 31, 1983 [GB] United Kingdom ................ 8302622
Jul. 26, 1983 [GB] United Kingdom ................ 8320164

[51] Int. Cl.$^4$ ...................... G01N 33/542; C12N 9/99
[52] U.S. Cl. ........................ 435/7; 435/184; 435/810; 436/510; 436/537; 436/814; 436/817
[58] Field of Search .................. 435/7, 23, 810, 184; 436/510, 537, 814, 817, 22, 23

[56] References Cited

U.S. PATENT DOCUMENTS

| | | |
|---|---|---|
| 3,817,837 | 6/1974 | Rubenstein et al. .................... 435/7 |
| 3,826,616 | 7/1974 | Laing .................... 436/814 |
| 4,134,792 | 1/1979 | Boguslaski et al. .................... 435/4 |
| 4,294,922 | 10/1981 | Heap .................... 435/7 |
| 4,463,090 | 7/1984 | Harris .................... 435/7 |
| 4,587,212 | 5/1986 | Baker .................... 437/7 |

FOREIGN PATENT DOCUMENTS 2102946A 2/1983 United Kingdom .................... 435/7
2120785A 12/1983 United Kingdom .

OTHER PUBLICATIONS

Friedrich et al. (1975), Occurence of Alpha Toxins in Raw Milk, Chem. Abstrts., 83(1): 1979d.
Sauer et al. (1981), Direct Enzyme Immunoassay of Progesterone in Bovine Milk, Chem. Abstr., 95: 1112580u.

Primary Examiner—Esther M. Kepplinger
Attorney, Agent, or Firm—Cushman, Darby & Cushman

[57] ABSTRACT

There is described an enzyme inhibitor labelled immunoassay for measuring the concentration of an analyte in a sample wherein the substrate for the enzyme forms at least a part of the sample. In a particular embodiment the sample comprises or consists of a milk sample and the inhibitor label is capable of inhibiting the activity of an enzyme capable of clotting milk. Examples are given of suitable inhibitors. The assay described may be used to measure the concentration of progestogens or oestrogens in milk using the techniques of heterogeneous or homogeneous enzyme inhibitor labelled immunoassay. The results of such an assay give an indication of the fertility of a milk producing domestic animal (e.g. a cow) and may be used to diagnose pregnancy of such an animal. Particular compounds for use in the assay are described, as is a kit of reagents for use in the assay.

18 Claims, 4 Drawing Figures

IMMUNOASSAY

The present invention relates to an enzyme inhibitor labelled immunoassay.

The general concept of enzyme immunoassay is described in many publications. For a general review see "Immunoassays: Clinical Laboratory Techniques for the 1980's", (Laboratory and Research Methods in biology and Medicine Vol. IV) ed. Nakamura R., Dito W. R., Rucker E.S. III published by A. R. Liss (1980)).

An enzyme immunoassay involves causing an antigenic analyte to compete in an immunochemical reaction with a known amount of antigen for a limited number of antibody binding sites. An enzyme is used to measure the proportion of the known amount of antigen which has become bound to the antibody, making it possible to calculate the amount of analyte present in a sample with reference to a standard assay result. There are in general two types of enzyme immunoassay, classified by the method employed for detecting the proportion of the known amount of antigen which has become bound to the antibody.

In the first type, heterogeneous enzyme immunoassay, either the known amount of antigen or the antibody is immobilised upon a solid phase, the other being labelled in some way. After reaction with a sample solution containing an antigenic analyte the solid phase may be physically removed from the sample solution and may be washed. A substrate for which the label has activity may then be placed in contact with the solid phase in order to estimate the amount of antibody bound to the known amount of antigen. An advantage of this type of enzyme immunoassay is that the physical separation and washing steps tend to increase the assay accuracy by removing extraneous substances introduced from the sample. A disadvantage of heterogeneous enzyme immunoassay is that the separation step is time consuming and requires a certain degree of manipulative skill.

In the second type, homogeneous enzyme immunoassay, measurement relies upon a change in the properties of a label when antibody binds to a hapten corresponding to the analyte marked with that label. The hapten has at least one antigenic determinant in common with the antigenic analyte and competes with the antigenic analyte for binding to a limited amount of antibody. In homogeneous enzyme immunoassay, separation of the bound and free labelled hapten is unnecessary since the proportion of bound labelled hapten can be estimated by measuring the relative change in the properties of the label. The lack of a separation step renders homogeneous immunoassay easier to perform, faster and cheaper than the corresponding heterogeneous immunoassay.

Despite a preference for the use of a homogeneous immunoassay the invention presently to be described may be conducted in the form of a heterogenous immunoassay.

One type of homogeneous immunoassay relies upon a change in specific enzyme activity when an antibody binds to an antigen labelled with an enzyme. This type of assay is known as a homogeneous enzyme labelled immunoassay. In homogeneous enzyme labelled immunoassay a hapten is attached to an enzyme in a position relative to an active site of the enzyme such that the enzymes catalytic action upon the substrate for which it has activity is substantially unimpaired. In use antibody may bind to the hapten and by this binding reduce or destroy the specific activity of the enzyme. The modulation of enzyme activity is thought to be caused either by steric hindrance; the antibody physically preventing the substrate engaging the active site on the enzyme; or in some cases by a restriction in the conformational flexibility of the enzyme, thereby preventing activity. There are some examples of homogeneous enzyme labelled immunoassay in which the hapten, when attached to the enzyme, impairs the enzyme's specific activity. The binding of an antibody to the hapten 'reactivates' the enzyme.

The techniques of homogeneous enzyme labelled immunoassay may be applied for example to the detection of drugs or narcotics in body fluids such as saliva, blood and urine (see British patent specification No. 1401297) and to the detection of steroids in milk (see copending published British patent application No. 2120785).

A second type of homogeneous immunoassay relies upon a change in enzyme inhibition activity when an antibody binds to an antigen corresponding to the analyte, labelled with an enzyme inhibitor. This type of assay is described hereafter as a homogeneous enzyme inhibitor labelled immunoassay. In homogeneous enzyme inhibitor labelled immunoassay a hapten is attached to an enzyme inhibitor molecule such that the resulting labelled hapten does not exhibit simultaneous heterobifunctional characteristics. That is, the molecule may bind either to an antibody to the hapten or to the active site of the enzyme for which the enzyme inhibitor has activity. The binding of antibody to the hapten effectively blocks binding of enzyme by the inhibitor resulting in a modification of the inhibitor activity of the inhibitor labelled hapten. The modification may be detected by measuring the inhibition of the activity of an enzyme.

A limitation of the first mentioned type of homogeneous immunoassay, the homogeneous enzyme labelled immunoassay, is that the enzyme labelled hapten is, in many cases, ditficult to produce reliably and reproduceably. The second type of homogeneous immunoassay, the homogeneous enzyme inhibitor labelled immunoassay, involves the use of inhibitors which are in many cases small and well defined chemical structures susceptible to chemical synthesis and the ready addition of hapten moieties.

The use and formulation of an enzyme inhibitor labelled immunoassay is described in U.S. Pat. No. 4134792. The specification describes an enzyme inhibitor labelled immunoassay for dinitrophenyl. The immunoassay described involves a conjugate molecule comprising a dinitrophenyl moiety and an acetazolamide moiety. The acetazolamide moiety has an inhibitory action upon the specific activity of carbonic anhydrase. The inhibitor may however be modulated by the formation of an immunocomplex between the conjugate molecule and antibody to dinitrophenyl.

A common feature of the known enzyme immunoassay techniques is the use of an enzyme having activity to a substrate unrelated to the sample to be analysed. Indeed in many cases the substrate itself requires careful preparation and the analysis of the enzymic reaction needs careful interpretation. This tends to complicate the assay protocol and renders it time-consuming and manipulatively complex.

According to a first aspect of the present invention we provide an enzyme inhibitor labelled immunoassay for measuring the concentration of an antigenic analyte in a sample wherein the substrate for the enzyme forms at least a part of the sample. According to a second aspect of the invention we provide an enzyme inhibitor labelled immunoassay for measuring the concentration of an antigenic analyte in a sample wherein the inhibitor label is an inhibitor capable of inhibiting the activity of an enzyme capable of clotting milk. Preferably we provide an enzyme inhibitor labelled immunoassay for measuring the concentration of an antigenic analyte in a sample comprising or consisting of milk wherein the inhibitor label is an inhibitor capable of inhibiting the activity of an enzyme capable of clotting milk. The preferred assay involves; the milk sample to be assayed for the antigenic analyte; a conjugate molecule comprising a moiety having at least one antigenic determinant in common with the antigenic analyte, the moiety being bonded to an inhibitor capable of inhibiting the activity of an enzyme capable of clotting milk such that the activity of the inhibitor is reduced or eliminated by the immunochemical binding of an antibody to the moiety, an antibody capable of forming an immunochemical bond to the conjugate molecule or to the antigenic analyte and an enzyme capable of clotting milk; the assay comprising the steps of allowing a competitive reaction to take place between antigenic analyte in the milk sample, the conjugate molecule and the antibody and determining the activity upon the milk sample of the enzyme capable of clotting milk.

The term "measuring" as used herein is to be taken to include both making a quantitative measurement of the concentration of an analyte in the sample and detecting whether an analyte is present in a sample above or below a predetermined concentration. Preferably the assay is used such that the presence or absence of milk clotting defines a predetermined end point.

The milk used in the assay may be milk of any mammal but is preferably the milk of a domestic milk producing animal such as a cow, a sheep or a goat and is most preferably the milk of a cow.

Preferably the enzyme used in the assay is chymosin. Chymosin is one of a number of proteolytic enzymes secreted by the fourth stomach (abomasum) of unweaned calves. It is the active ingredient of rennin (also known as rennet) and has, for hundreds of years, been used in the production of cheese. The natural substrate of chymosin is the protein casein which is the major solid component of milk. In milk, casein exists as a stable colloid of casein molecules. The addition of chymosin to milk catalyses the cleavage of casein to form proteins which are not stable as a colloid. The cleavage results in an agglutination of the protein molecules; an effect which may be observed macroscopically as clotting. The chymosin may be natural chymosin isolated from calves or may be chymosin or a chymosin analogue produced by a host organism modified by recombinant DNA techniques (see copending published British patent application No. 2100737). Other milk clotting enzymes which may be used in the assay of the present invention include proteolytic enzymes such as pepsin and its analogues and enzymes derived from fungal strains such as *Mucor pusillus, Mucor meihei* and *Endothia parasitica*.

The inhibitor used to produce the inhibitor labelled hapten must be capable of reducing or eliminating the specific activity of the enzyme capable of clotting milk and must be such that when bound to a hapten its inhibition activity is reduced by the binding of an antibody to the hapten. Many such inhibitors are known to the art (see Bibliography at the end of this specification).

The inhibitor may be selected from one of four groups of inhibitors.

(The amino acid sequences given hereafter use standard notation for amino acid residues. (e.g. val=valyl ala=alanyl iva=isovalyl etc.). The amino acid statine has the formal chemical name 4(S)-amino, 3(S)-hydroxy, 6 methylheptanoic acid).

The first group comprises the polypeptide pepstatin:

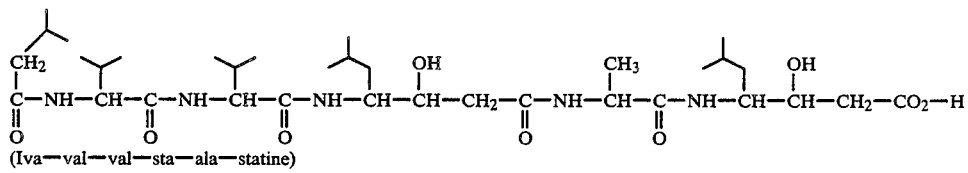
(Iva—val—val—sta—ala—statine)

and analogues of pepstatin, example of which are N-acetyl-val-val-sta-ala-statine, N-acetyl-val-sta-ala-statine, N-acetyl-statine, N-acetyl-ala-statine, N-acetyl-val-statine, statine, ala-statine,

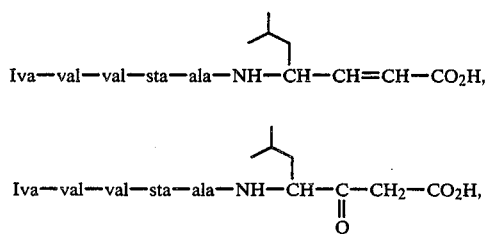

N-acetyl-sta-ala-NH$^i$C$_5$H$_{11}$, Iva-sta-ala-NH$^i$c$_5$H$_{11}$, Iva-val(3S,4S)-sta-ala-NH$^i$C$_5$H$_{11}$, Iva-val-(3R,4S)-sta-ala-NH$^i$C$_5$H$_{11}$, Iva-val-(3S,4S)-(4-amino-3-hydroxy-5-phenylpentanoic acid)-ala-NH$^i$C$_5$H$_{11}$, Iva-val-(3S,4S)-(4(S)-amino-6-methylheptanoic acid)-ala-NH$^i$C$_5$H$_{11}$, Iva-val-sta, Iva-val-val-sta,

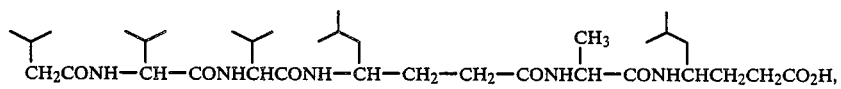

Iva-val-statone-ala-NHiC$_5$H$_{11}$, and Iva-val-(4(S)-amino-6- methylheptanoic acid)-ala-NHiC$_5$H$_{11}$.

The pepstatin or pepstatin analogue may be further modified by the inclusion of a C-terminal group, especially one selected from the group; -arg-OMe, -asp, -glu, -asp-arg, and -gly-lys-lys. The addition of -gly-lys-lys to the C-terminal of pepstatin or pepstatin derivative advantageously increases the water solubility of the derivative.

The second group comprises synthetic polypeptides having the general structure

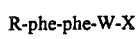
R-phe-phe-W-X wherein X is a C-terminal D-amino acid radical, W is an amino acid radical and R is an amino acid radical or a polypeptide radical having two or more amino acids. Preferably X is D-leucine, W is valine and R is selected from the group pro-,D-phe-pro-,glu-D-phe-pro-,D-glu-D-phe-pro-.

The third group comprises synthetic polypeptides having the general structure

H-his-pro-phe-his-Y-val-tyr-OH wherein Y is

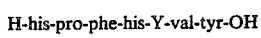
—CH—CH$_2$—NH—CH— or —CH—CH$_2$—NH—CH—

The fourth group comprises synthetic polypeptides having the structure

P-ser-Z-ala-Q, P-val-Z-val-Q or P-asp-Z-ala-Q wherein Z is statine or Z is a diradical of the general formula

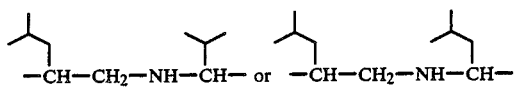

wherein R$_1$ is —CH$_2$—NH—

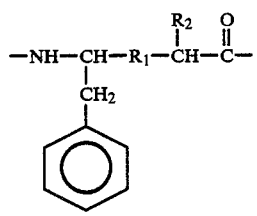

(a retroinverso peptide analogue) and R$_2$ is —CH$_2$CH$_2$CH$_2$CH$_3$, —CH$_2$CH$_2$SCH$_3$ or —H, and wherein P is selected from A-, his-A-, pro-his-A, his-pro-his-A-, pro-his-pro-his-A, his-pro-his-pro-his-A, and arg-his-pro-his-pro-his-A, wherein A is a leucine or valine radical, and wherein Q is selected from -B, -B-pro, -B-pro-pro, -B-pro-pro-lys, -B-pro-pro-lys-lys, and -B-pro-pro-lys-lys-asn, wherein B is an isoleucine or leucine radical.

Preferably R$_1$ is —CH$_2$—NH— or

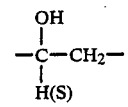

Preferably the inhibitors of the fourth group are synthetic polypeptides of the general formulae,
leu-asp-Z-ala-ile-pro-pro-lys-lys,
his-leu-asp-Z-ala-ile-pro-pro-lys-lys,
leu-ser-Z-ala-ile-pro-pro-lys-lys or
his-leu-ser-Z-ala-ile-pro-pro-lys-lys,
wherein Z is as previously defined. Preferably Z is statine.

The following inhibitors of the fourth group are thus especially preferred
his-leu-ser-sta-ala-ile-pro-pro-lys-lys
leu-ser-sta-ala-ile-pro-pro-lys-lys The C-terminal and/or the N-terminal amino acid of any of the inhibitors may be substituted. For example the C-terminal amino acid may be esterified and/or the N-terminal amino acid may be acylated.

The basis of the enzyme inhibitor labelled immunoassay of the present invention is a competitive immunological reaction set up between the analyte, a labelled hapten (also referred to as a conjugate molecule) and a limiting amount of antibody. The antibody, which may be a monoclonal or a polyclonal antibody, has specificity for one or more determinants common to both analyte and hapten. The hapten is labelled by conjugation with a molecule capable of reducing the activity of an enzyme capable of clotting milk. The resulting conjugate molecule alone is also capable of reducing the activity of an enzyme capable of clotting milk. The labelled hapten is so constructed that when antibody binds to the hapten the inhibitor is deactivated. In this way the proportion of labelled hapten left unbound to antibody in an assay sample can be determined by its effect upon the milk clotting activity of an enzyme capable of clotting milk added to or included in the sample of milk.

When analyte is present in the milk sample under test, following reaction of the assay components, a significant proportion of labelled hapten remains free of antibody. The free labelled hapten may then combine via its inhibitor label with enzyme added to or included in the sample, thereby deactivating the enzyme. The activity of the enzyme may be readily tested by the addition to, or inclusion in, the sample of a quantity of milk. When analyte is present in a sample under test no clotting will be observed.

When analyte is not present in the sample under test, following reaction of the assay components a significant proportion of labelled hapten becomes bound to antibody. The inhibitor label of the hapten is deactivated resulting in little or no deactivation of enzyme activity. When analyte is absent or present in very low concentrations, clotting of milk included in or added to the sample will be observed.

The assay reagents and sample may be mixed together in any order or combination.

In a particular application of the present invention the homogenous enzyme inhibitor labelled immunoassay is used to determine the concentration of hormones naturally present in cows milk.

The economics of dairy farming require the production of one calf per cow per year. This is necessary in order to ensure a satisfactory and constant supply of milk from a dairy herd. The calving index of a cow is the number of days that pass between successive calvings. Thus the ideal calving index is 365 days and extensions beyond this are likely to affect adversely the profitability of a cow. It is essential to good herd management that the correct time is chosen for insemination and that a check is available subsequently to ensure that conception has occurred.

Traditionally the correct time for arranging for insemination of a cow was judged by the herd manager on the basis of the behaviour of the cow. The diagnosis of pregnancy relied either upon a study of the cows subsequent behaviour or upon a rectal examination by a veterinary surgeon some 10 to 15 weeks after insemination. The necessary delay before making a physical examination often is considerable. These traditional methods are still extensively used today.

It is known that the level of progestogen in the milk of lactating dairy cows reflects ovarian activity. The cow is a polyoestrus animal and ovulates spontaneously in an oestrus cycle having a period of approximately twenty one days. The level of a particular progestogen, progesterone, in milk varies cyclically over the period between successive ovulations. The concentration of progesterone in a cow's milk builds up gradually after oestrus from a very low level to a plateau of about 25 ng/ml milk and drops sharply to a very low level immediately before the next ovulation. It is further known that if a successful insemination is carried out on the day of oestrus, the level of progesterone in milk remains high throughout the pregnancy.

British patent specification No. 1402263 describes a method of diagnosing pregnancy in an inseminated milk-producing domestic animal in which an assay for progestagen is carried out on the milk of the animal in order to ascertain whether the progestogen concentration is varying cyclically or is fixed at high value. The latter result is indicative of pregnancy.

The methods of assay described in British patent specification No. 1402263 are competitive protein binding assay and radioimmunoassay. Both these assays require skilled work and specialised equipment, and often involve considerable time delays.

An alternative method of diagnosing pregnancy in cows is described in British patent specification No. 2040043. The level of an oestrogen metabolite, oestrone sulphate, in milk increases gradually during pregnancy and gives a further indication of successful insemination. British patent specification No. 2040043 describes a method of measuring the level of oestrone sulphate in milk using an enzyme-linked immunoassay involving a colourimetric determination of end point. Such an assay involves less skill on the part of the operator but nevertheless is time-consuming and complex.

Many countries now have commerical laboratories which will assay milk samples for progesterone. The technique most commonly used by such laboratories is radioimmunoassay. This inevitably involves delay, and if the assay is required for othe purposes of detecting oestrus the result of the assay may arrive too late for successful insemination.

There is therefore a great need in the dairy industry for a simple and effective assay for progestogens, progestogen metabolites, oestrogens and oestrogen metabolites such that the herd manager can perform a 'cow side' test for oestrus or for pregnancy. Copending published British patent application No. 2120785 describes an enzyme labelled immunoassay for use in testing for oestrus or pregnancy in domestic milk producing animals.

According to a third aspect of the present invention we provide an enzyme inhibitor labelled immunoassay for measuring the concentration of a steroid in a sample wherein the steroid is selected from the group consisting of a progestogen, a progestagen metabolite, an oestrogen and an oestrogen metabolite. Preferably the sample is a sample of milk from a domestic milk producing animal most preferably a cow. Preferably the steroid is progesterone, oestrone sulphate or an analogue of either.

A number of diagnostic tests to be applied to cows are made possible by the assay of the present invention.

According to a fourth aspect of the invention oestrus in a milk-producing domestic animal such as a cow, a sheep or a goat is detected by monitoring the level of progesterone in the milk of the animal using the assay of the present invention. The assay may be used, for example, to indicate when the level of progesterone in the milk of the animal falls below a predetermined value. In the general method, using a homogeneous enzyme inhibitor labelled immunoassay, a molecule of progesterone (or a molecule having at least one antigenic determinant in common with progesterone) is chemically bonded to an inhibitor molecule. In performing the assay a mixture is prepared consisting of the progesterone inhibitor conjugate molecule, a limiting amount of antibody to progesterone and a sample of milk including inter alia the progesterone and casein. A competitive equilibrium is established in which the free progesterone and the progesterone inhibitor conjugate molecule compete for the limiting amount of antibody. Chymosin may be included in the initial mixture or may be added after equilibrium has been reached. If the progesterone is absent or present only in low concentration in the milk sample a significant fraction of the antibody will bind to the progesterone inhibitor conjugate. The action of the inhibitor upon the chymosin will be impaired and clotting of the milk will be observed. In the alternative, if progesterone is present in the milk sample a significant fraction of the antibody will become bound to the progesterone in the sample. This will result in the presence of non-immunocomplexed progesterone inhibitor conjugate in the sample, the chymosin will therefore be substantially inactive and no clotting of the milk sample will be observed. The sensitivity of the assay may be adjusted by altering the concentrations of the various reagents used in the assay. It is also possible to adjust the sensitivity of the assay by changing the order in which the reagents are admixed. For example, the addition of the antibody to the milk sample before the progesterone inhibitor conjugate will affect the sensitivity. In general a level of progesterone below 4 ng/ml is indicative of the onsent of oestrus.

In a practical situation the dairyman can take a sample of milk from a cow whilst in the dairy. The sample may be placed in a suitable receptacle and the various reagents may be added or in the alternative the sample may be added to the reagents in a suitable receptacle. Following initial mixing the presence or absence of clotting may be observed. When using the assay for progesterone a change in the result from non-clotting to clotting may be taken as an indication of the onset of oestrus, indicating as it does that the concentration of progesterone in the cow's milk has fallen below a predetermined level.

We further provide, in a fifth aspect of the invention, a method for detecting pregnancy in a milk-producing domestic animal, comprising using an enzyme inhibitor labelled immunoassay according to the invention to monitor the concentration of progesterone in the milk of the animal, pregnancy being indicated by the lack of a drop in the concentration of progesterone below a predetermined concentration at a time when oestrus would be expected.

We further provide, in a sixth aspect of the invention, a method for detecting pregnancy in a milk-producing domestic animal, comprising using an enzyme inhibitor labelled immunoassay according to the invention to monitor the concentration of oestrone sulphate in the milk of the animal, pregnancy being indicated by a concentration of oestrone sulphate above a predetermined concentration.

There is currently great interest in the dairy industry in the detection of a substance known as aflatoxin $M_1$. The aflatoxins are mycotoxins originating from fungal contamination of certain cattle feeds. The compounds and their metabolites are mutagenic, carcinogenic and teratogenic. Aflatoxin $M_1$ is one of aflatoxin metabolites and is of particular interest as it retains a very high toxicity and appears in the milk of cattle which have consumed contaminated feed. Clearly there is a need for a fast and reliable assay to ensure that milk containing aflatoxins and in particular aflatoxin $M_1$ does not reach consumers. Aflatoxin $M_1$ is of a similar molecular size to the steroids and the acceptable concentrations in milk are similar to those of steroid metabolites naturaly found in milk.

According to a seventh aspect of the invention we provide a method for monitoring the concentration of an aflatoxin metabolite, preferably aflatoxin $M_1$ in the milk of milk producing domestic animals comprising using an enzyme inhibitor labelled immunoassay of the invention to measure the concentration of aflatoxin in the milk of the animal.

Preferably the above methods are applied in relation to a cow and cow's milk.

According to an eighth aspect of the present invention we provide an inhibitor for an enzyme capable of clotting milk wherein the inhibitor is a synthetic polypeptide of the fourth group of inhibitors described above.

According to a ninth aspect of the invention we provide a conjugate molecule comprising a hapten labelled with an inhibitor capable of inhibiting the activity of an enzyme capable of clotting milk. The labelled hapten is constructed such that when antibody binds to the hapten the inhibitor is substantially deactivated. The hapten may be any antigenic molecule, those steroids described with reference to the fourth, fifth and sixth aspects of the present invention and the toxin described with reference to the seventh aspect of the present invention being particularly preferred. The inhibitor may be any inhibitor described above and is preferably selected from the fourth group of inhibitors described above.

In particular, with reference to the fourth and fifth aspects of the invention, a preferred conjugate molecule is selected from the group

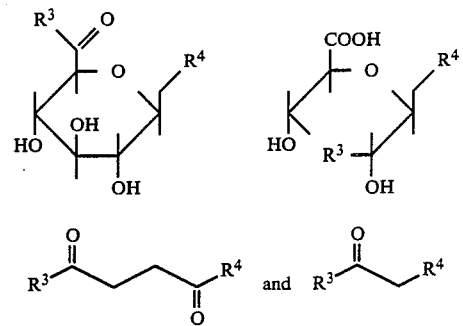

wherein R3 is a radiacl or diradical derived from any one of the inhibitors described above, and R4 is aflatoxin $M_1$

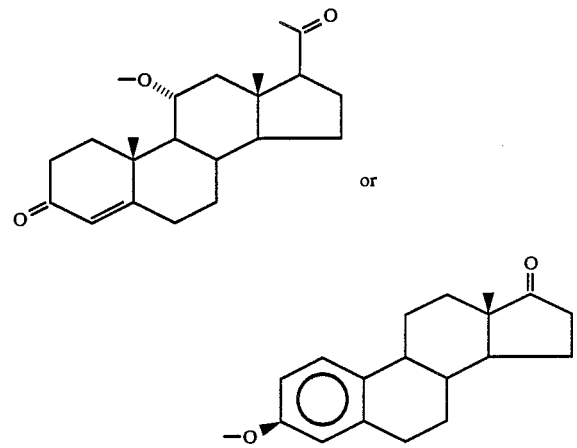

Particularly preferred is a conjugate molecule having as R3 any of the inhibitors of the fourth group of inhibitors described above.

Suitable conjugate molecules include

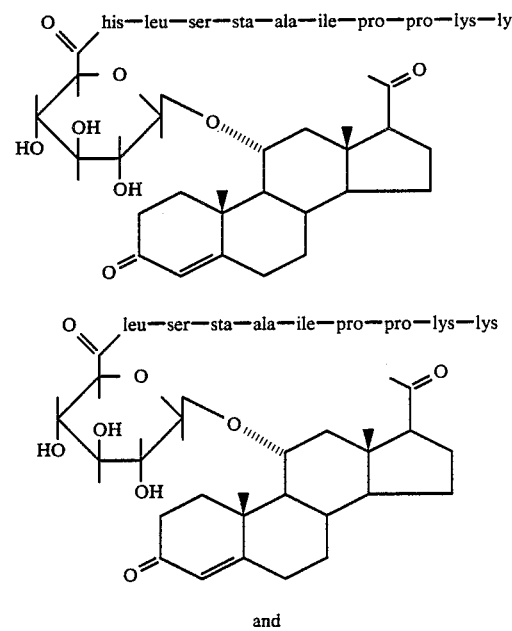

and

-continued

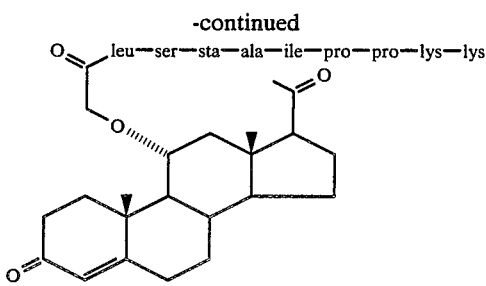

In an assay of the third aspect of the invention it is preferred that the progesterone antibody has been raised against a progesterone immunogen where the progesterone hapten has been linked to a carrier protein via a C-11α substituent According to a tenth aspect of the invention we provide a reagent kit for performing an immunoassay of the present invention, the kit comprising, separately or in combination, a conjugate colecule of the ninth aspect of the invention, an antibody capable of binding to an antigenic determinant of the conjugate molecule and an enzyme capable of clotting milk. The kit may comprise the reagents combined together in a suitable container for example in an assay receptacle. Alternatively the kit may comprise the reagents packed separately or combined in pairs with a third separately packaged. The reagents may be in a stabilised form, for example in a lyophilised form.

Some embodiments of the present invention are now described as examples, with reference to the accompanying drawings in which.

Figure 1:
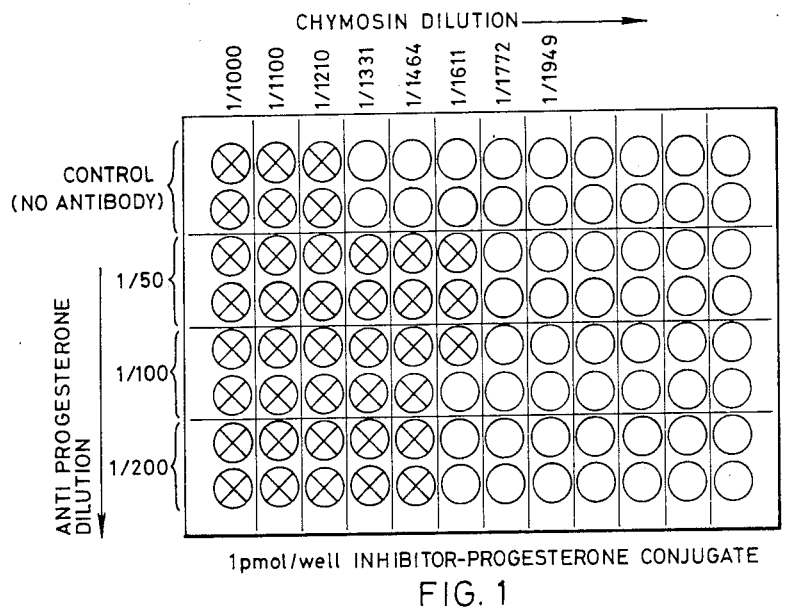
FIG. 1 shows the results of a "checkerboard" titration on a microtiter plate indicating the effect upon milk samples of various dilutions of chymosin and anti-progesteron in the presence of a chymosin inhibitor progesterone conjugate molecule.

In all the figures the circles represent wells in the microtiter plate. Where a cross appears within a circle a milk clot was evident.

MATERIALS

1. Antibodies

Polyclonal antisera to progesterone were obtained from the Milk Marketing Board, Veterinary Laboratories, Cleeve House, Lower Wick, Worcester, England and from Guildhay Antisera, Division of Clinical Biochemistry, Department of Biochemistry, University of Surrey, Guildford, Surrey, England. The antiserum from the Milk Marketing Board had been raised against the immunogen progesterone-11α -hemisuccinyl- bovine serum albumin and the Guildhay antiserum raised against progesterone-11α -hemisuccinyl-ovalbumin.

Monoclonal progesterone antibody was obtained from Dr. Wang of the Imperial Cancer Research Fund Laboratories, Lincolns Inn, London, England. It had been raised against the immunogen progesterone-11 -hemisuccinyl-bovine serum albumin according to the method of V. E. Fantl, D. Y. Wang and R. E. Knyba, *J. Steroid Biochem*, 1982, 17, 125–130. The monoclonal antibody of choice for use in the specific assay described below is designated 11P12 in the above mentioned publication.

2. Chymosin

Calf Chymosin (EC 3.4. 23.4) was obtained from Sigma Chemical Co. Ltd., Fancy Road, Poole, Dorset, England or from recombinant prochymosin produced in *E. coli* supplied by Celltech Ltd., 244–250 Bath Road, Slough, Berkshire, England. The chymosin was purified by affinity chromatography using diaminodipropylamine-pepstatin Sepharose CL-6B obtained from Pierce Chemical Company, Rockford, Ill., 61105, U.S.A. by the method of H. Kobayashi and K. Murakani, *Agric. Biol. Chem.* 1978, 42 (12), 2227–2231.

3. Steroids

Progesterone-11α-glucuronide was synthesised according to the method of J. E. T. Corrie, W. M. Hunter and H. S. Macpherson, *Clin Chem.*, 1981, 27 594–599. Progesterone-11α-carboxymethyl ether was synthesised according to the method of P. N. Rao, K. M. Damodaran, P. H. Moore JR., C. Desjardins and P. Garza, *J. Steroid Biochem*, 1982, 17, 523–527. Tritiated progesterone was obtained from Amersham International Plc. White Lion Road. Amersham. Buckinghamshire, England.

4. Chromogenic Peptide Substrates

Chromogenic peptide substrates were supplied by Dr. B. M. Dunn, Department of Biochemistry and Molecular Biology, University of Florida, Gainesville, Fla., U.S.A.

5. Milk Substrate

Substrates used to demonstrate the immunoassay principle were prepared from either commercial preparations of powdered, de-fatted milk or whole cows milk, obtained from cows which had recently calved (7 to 14 days past-calving) or from cows which had been observed to be at oestrus. Skimmed-milk substrate solutions were prepared by dissolving the powdered milk in 40 mm calcium chloride to give a concentration of 24%(w/v) and then passing the milk solution through SEP-PACK C18 cartridges prewetted with methanol (5 ml) and water (5 ml) at 10 ml of skimmed milk per cartridge. (SEP-PACK cartridges were obtained from Waters Associates, Maple Street, Milford, MA 01757, U.S.A.). The reverse-phase treatment was necessary to remove endogeneous steroids from the skimmed-milk. Cows milk was supplemented by addition of crystalline calcium chloride to a concentration of 40 mM. In both cases the substrate solutions were incubated at 37° C. for at least 15 minutes prior to use.

6. Chymosin Assay Buffer 0.013 M 2-[N-Morpholino ethanesulphonic acid (MES) buffer at pH6.0.

7. Radioimmunoassay Buffer 0.05 M phosphate pH 7.5 containing, 0.9% calcium chloride 0.1% gelatin and 0.1% sodium azide preservative.

8. Microtiter Plates

The immunoassay system was demonstrated by carrying out the assay in the wells of polyvinylchloride, U-well, microtiter plates. These were obtained from Dynatech Limited, Duax Road, Billingshurst, Sussex, England.

9. Incubator

The assays to be described were carried out at 37° C. using a microtiter plate incubator (Dynatech Ltd.).

10. Other Reagents

These were obtained from Sigma Chemical Co. Ltd.

METHODS

1. Preparation of Peptide inhibitors and Progesterone inhibitor conjugates

1.1 Inhibitor Synthesis

Two synthetic inhibitors of the fourth group of inhibitors were prepared.

The inhibitors include the amino acid statine (4(S)-amino, 3(S)-hydroxy, 6 methylheptanoic acid) which was prepared in a protected form by the synthesis described in the scheme given below. In the scheme, Z is a benzyloxycarbonyl protecting group, DIBAL represents diisobutylaluminium hydride, THF represents tetrahydrofuran THP represents tetrahydropyranyl and FMOC represents 9-fluorenylmrthoxycarbonyl.

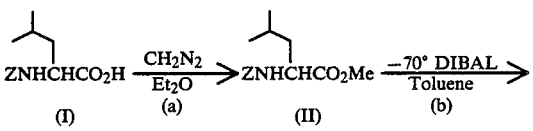

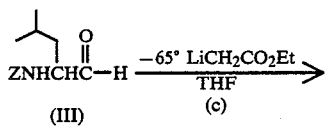

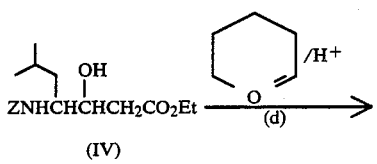

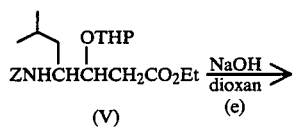

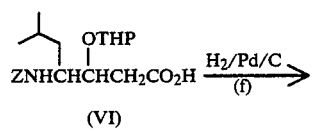

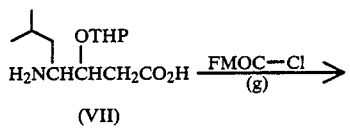

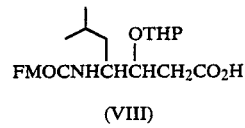

The reactions described in above scheme were carried out as follows:

(a) To an ice-cooled solution of Z-S-leucine I (29 g, 0.11 mol) in ether (200 ml) was added a solution of diazomethane in ether (6 g, 0.11 mol). After the evolution of nitrogen had ceased, the mixture was concentrated in vacuo to an oil (compound II). Compound II was used in the next reaction without purification.

(b) To a vigorously stirred solution of compound II (14.49 g, 48.9 mmol) in dry toluene (210 ml), was added a 1M solution of diisobutylaluminium hydride (DIBAL) (124 ml, 124 mmol) in hexane at −70° C. under nitrogen. After 6 mins, methanol (12 ml) was added followed immediately by saturated Rochelle salt solution (500 ml). The reaction mixture was allowed to warm up to room temperature and was then extracted with ether (3×300 ml). The organic layers were sequentially washed with saturated sodium chloride solution, dried over sodium sulphate and concentrated to an oil. The yield of compound III was 7.9 g. The compound was stored at −20° C. and used as soon as possible without further purification.

(c) To diisopropylamine (19.2 ml, 137 mmol) in dry tetrahydrofuran (THF) (45 ml) in a dry ice/chloroform bath under nitrogen was added 1.6M n-butyllithium in hexane (85.62 ml, 137 mmol) by syringe. After one hour, the bath was replaced with a dry ice/ethanol bath and dry ethyl acetate (13.4 ml, 13.7 mmol) was added slowly whilst keeping the temperature at about −70° C. After the addition, the reaction mixture was left to stir for 15 minutes at which time compound III (22.8 g, 92 mmol) in dry THF (90 ml) was added whilst keeping the temperature below −65° C. The reaction mixture was stirred for 5 minutes at which time 1M hydrochloric acid (300 ml) was added and the reaction mixture was allowed to warm up to room temperature and was extracted with ethyl acetate (3×200 ml). The organic layers were sequentially washed with saturated sodium chloride solution (1 liter), dried over sodium sulphate and concentrated to an oil of crude material. The yield containing compound IV was 3g. The material was purified twice by silica gel chromatography.

First Chromatography Conditions 31 g of the crude material was applied onto 500 g of Merck 9385 silica gel. (2 liters chloroform, followed by 2 liters chloroform/ethyl acetate (95:5)). This yielded 26 g of the unseparated two isomers of compound (IV) (3R, 4S and 3S, 4S) having an Rf of 2.0 (20% ethyl acetate in toluene).

Second Chromatography Conditions 12 g of partially purified compound IV was applied onto 200 g of Merck 9385 silica gel. (1 liter toluene- /ethyl acetate (95:5) followed by 1 liter toluene/ethyl acetate (9:1) followed by 1 liter ethyl acetate (85:15) followed by 2 litres toluene/ethyl acetate (4:1)). Sixty 50 ml fractions were collected.

2.4g of the required isomer of compound IV (3S,4S) with an Rf of 0.23 was separated from 1.1 g of the unrequired isomer (3R, 4S) having an Rf of 0.17 (Elution with 20% ethyl acetate in toluene). (d) To compound IV (2.9 g, 8.6 mmoles) in dry dioxan (30 ml) was added, with stirring, dihydropyran (4 ml, 51.6 mmoles) followed by about 2 mg of p-toluenesulphonic acid monohydrate. After two hours stirring in the dark H.P.L.C. showed that the reaction was complete. The HPLC was conducted using an ultrasphere reverse phase HPLC column (30 cm×4 mm). Flow 1 ml min$^{-1}$; Solvent A: water; Solvent B: methyl cyanide; λ:260 nm. (0min-60% A, 40% B, 15 min 20% A, 80% B; 20 min-20% A., 80% B). The reaction was complete when the peak due to compound IV, with a retention time of 11 minutes, disappeared. The reaction mixture was well shaken with saturated aqueous sodium hydrogencarbonate (300 ml) and extracted with dichloromethane (3×200 ml). The organic layer was washed with saturated aqueous sodium hydrogencarbonate (1×300 ml), and water (1×200 ml) and was concentrated to an oil. The oil was placed in a high vacuum (about 10-1Torr) overnight to remove excess dihydropyran. The yield of compound V (with dioxan still present) was 3.8 g. The compound was used without further purification. (e) To compound (V) (about 2.7 g, about 6 mmoles) in dioxan (35 ml) was added with stirring 1M aq. sodium hydroxide (35 ml). A clear solution formed after 30 minutes and HPLC showed reaction to be complete after 2 hours. The conditions and protocol of HPLC were as in (d) above 20 μl of the reaction mixture was mixed with 2 μl of Aristar glacial acetic acid and 10 μl of the mixture thus formed was injected onto the column. The reaction was complete when the peak due to compound V, with a retention time of 17 minutes, disappeared. Water (50 ml) was added and the aqueous solution was washed with ether (3×50 ml), ethyl acetate (2×50 ml) and its pH was adjusted with concentrated hydrochloric acid to pH 6.00. The resultant oily solution was *immediately* extracted with ethyl acetate (4×75 ml). Immediate extraction is necessary because of the lability of the tetrahydropyran (THP) group. The organic layer was washed with water (1×50 ml), dried over sodium sulphate and evaporated to an oil.

The yield of compound VI was 1.92 g. The compound was used without further purification. (f) To compound (VI) (1.920 g, 4.7 mmoles) in methanol (25 ml) was added 5%Pd/C catalyst (0.50 g). Hydrogen was passed through the mixture, with stirring for one hour. The reaction mixture was filtered through celite and washed with 10% water in methanol (50 ml). The collected filtrate was concentrated to a solid. TLC ethanol/hexane, 2:1 v/v developed with a ninhydrin spray gave a product spot at Rf 0.13.

The yield of compound VII was 1.11 g. The compound was used without further purification. (g) To a stirred solution of compound VII (0.526 g, 2 mmol) in 10% (w/v) aq. sodium carbonate (5.4 ml) and dioxan (2 ml), was added 9-fluorenylmethoxycarbonyl chloride FMOC-Cl (0.544 g, 2.1 mmol) in dioxan (5 ml) over a period of 20 minutes. During this addition more 10% (w/v) aq. sodium carbonate (13 ml) was added over the same period in order to maintain a clear solution. After 60 minutes stirring, water (20 ml) was added and the mixture was concentrated to about half its original volume. More water (200 ml) was added before the mixture was washed with ether (4×200 ml). The aqueous layer was adjusted carefully with hydrochloric acid to pH6.5 and then immediately extracted with ethyl acetate (4×150 ml). The organic layer was washed with water (100 ml), dried over sodium sulphate and concentrated to a solid (0.740 g).

The product compound VIII was purified by reverse phase chromatography, under the following conditions: 2.5 cm×50 cm column packed with Lichroprep RP18 30% methanol/water - 100% methanol over 2 liters. 100% methanol 1 liter
20 ml fractions were collected.

Fractions 101–118, which contained product, were pooled, concentrated to half its original volume, added to water (500 ml) and extracted with dichloromethane (3×500 ml). The organic layer was washed with water (100 ml), dried over sodium sulphate and concentrated to a solid (0.450 g).

Nmr (CDCl$_3$): T 9.0 (6H,d, (CH$_3$)2CH2); 8.6–8.0 (9H,M,THP); 7.4 (2H,d, C$\underline{H}$2—CO$_2$H); 6.5 (2H, d, C$\underline{H}$2OC($\overline{O}$)); 2.7–2.0 (8H,$\overline{M}$ (C6H4)2CH2; 1.1 (1H, 6$\overline{brs}$, CO$_2$H).

The protected statine produced by the above steps (a)–(g) was used in the preparation of a polyamide supported, partially protected decapeptide IX essentially by the method described by Atherton et al (Proc. 17th European Peptide symp., eds. Blaha, K. and Malon, P. pp 241-246 (1982)).

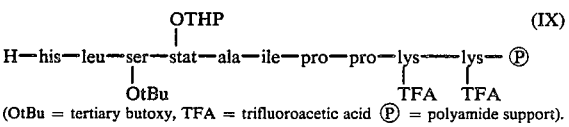

(OtBu = tertiary butoxy, TFA = trifluoroacetic acid Ⓟ = polyamide support).

A polyamide supported, partially protected nonapeptide X was also prepared, using the same method.

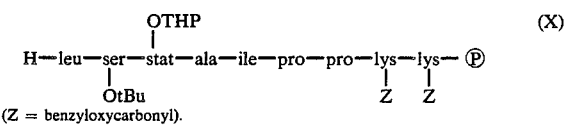

(Z = benzyloxycarbonyl).

Compounds X and IX are inhibitors of the activity of chymosin.

2.2. The inhibitors produced by the processes described in 2.1 above were conjugated to progesterone moieties in the following reactions

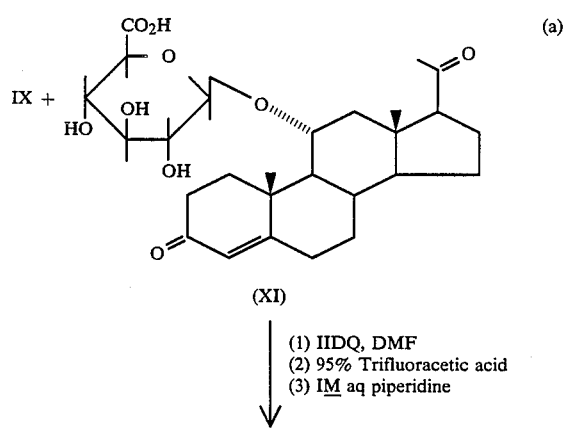

-continued

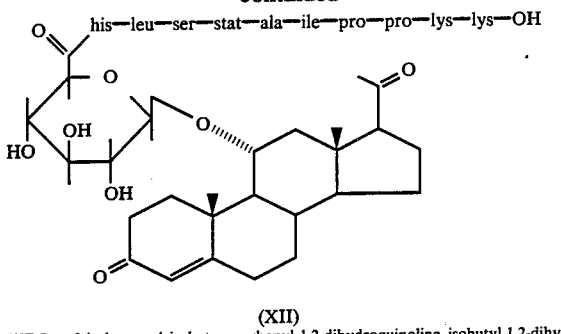

(XII)

(IIDQ = 2-isobutoxy-1-isobutoxycarbonyl-1,2-dihydroquinoline, isobutyl 1,2-dihydro-2-isobutoxy-1-quinolinecarboxylate. DMF = Dimethylformamide)

Compound IX (200 mg, about 0.04 mmol) was prewashed with t-amyl alcohol, aqueous hydrochloric acid, pH4.5 (2×3 min), t-amyl alcohol, DMF, 10% diisopropylethylamine in DMF (2×3 min) and DMF. To the washed compound IX in DMF (2 ml) was added compound XI (0.084 g, 0.16 mmol) and IIDQ (0.052 ml, about 0.180 mmol). A ninhydrin test of the polyamide resin showed the reaction to be complete after 48 hours. The product was cleaved from the resin with 95% trifluoracetic acid and deprotected with IM aqueous piperidine. The product XII was purified by cation exchange chromatograph on a Synchropak CM 300 column. The yield of compound XII was 4 mg. The compound was homogeneous on reverse phase HPLC ($\mu$ Synchropak C18) and FAB mass spectroscopy gave the correct (M+H)+ ion of 1635 with the corresponding correct fragmentions.

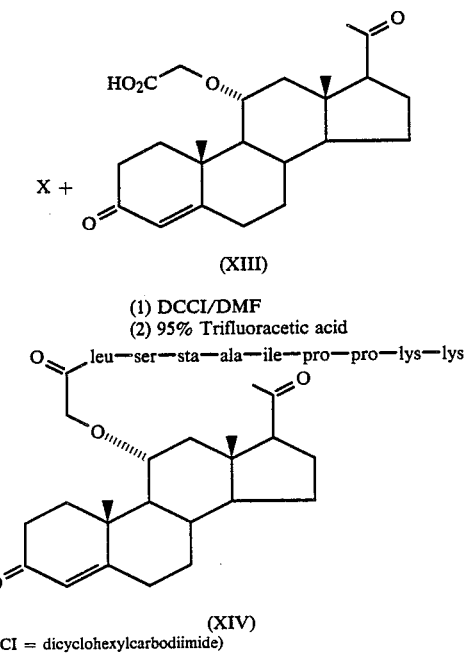

(DCCI = dicyclohexylcarbodiimide)

Compound XIII (0.059 g, 0.15 mmol) was dissolved in 5 ml dichloromethane and DCCI (0.016 g, 0.075 mmol) was added. The reaction mixture was left for 1 hour after which time the solvent was removed in vacuo. The residue was dissolved in DMF (3 ml), filtered and added to compound X (180 mg). A ninhydrin test of the polyamide resin showed the reaction to be complete after 40 minutes. The product was deprotected and cleaved from the resin with 95% trifluoracetic acid. The product XIV was purified by cation exchange chromatography on a Synchropak CM 300 column and further purified on reverse phase Synchropak RP-P. The yield of compound was confirmed by FAB mass spectroscopy which showed an intense spectrum with a strong quasi molecular ion (1380).

2. Testing of Inhibitors and Progesterone-Inhibitor conjugates for enzyme inhibitor activity Enzyme inhibition data was obtained using synthetic peptide substrates containing a chromophoric nitrophenylalanine residue in the position of the scissile bond so that hydroysis can be followed spectrophotometrically. Hydrolysis was followed at 300 nm and the substrate can be used at any pH value (usually between 2-6) at which the enzyme is active. Kinetic parameters for the hydrolysis of a chromogenic peptide substrate by different types of mammalian aspartic proteinases have been reported J. Kay, M. J. Valler and B. M. Dunn, Naturally-occurring inhibitors of Aspartic Proteinases in Proteinase Inhibitors; N. Katunuma, H. Umezawa and H. Holzer Eds., 1983 Springer-Verlag, Berlin (in press).

3. Testing of Progesterone derivatives and Progesterone-inhibitor conjugates for immunoreactivity A radioimmunoassay employing tritiated progesterone and dextran coated charcoal separation of bound and free progesterone was used to assess the immunoreactivity of progesterone derivatives and progesterone-inhibitor conjugates with the monoclonal and polyclonal antisera, by the method of R. B. Heap, R. J. Holdsworth, J. E. Gadsby, J. A. Laing and D. E. Walters, Brit. Vet. J. 1976, 132, 445-464.

Table 1 (below) summarises the enzyme inhibition and immunoreactivity data for the peptide derivatives and progesterone conjugates used in the invention.

TABLE 1

| Progesterone Derivative or Peptide Analogue (see key) | Immunoreactivity | | Enzyme Inhibition Data | |
|---|---|---|---|---|
| | Monoclonal 11P12 | Polyclonal | Enzyme | pH  Ki ($\mu$m) |
| I | 151% | 92.1% (18/3) | | |
| II | 77.4% | | | |
| III | | | Endothia Parasitica | 3.1  0.01 |

TABLE 1-continued

Progesterone

| Derivative or Peptide Analogue (see key) | Immunoreactivity | | Enzyme Inhibition Data | | |
|---|---|---|---|---|---|
| | Monoclonal 11P12 | Polyclonal | Enzyme | pH | Ki (μm) |
| | | | Protease | | |
| IV | | | Endothia | 3.1 | 0.006 |
| | | | Parasitica | | |
| | | | Protease | | |
| V | 31.8% | 9.5% (18/3) | Chymosin | 6.0 | 0.052 |
| | | | Endothia | 6.0 | 0.04 |
| VI | 3.8% | 16.4% (18/3) | Chymosin | 6.0 | 0.02 |
| | | 34% (HPS 53IIb) | Endothia | 6.0 | 0.47 |
| VII | 17.1% | 33.6% (18/3) | Chymosin | 6.0 | 0.0067 |
| | | 17.4% (HPS 645IIc) | Endothia | 6.0 | 0.026 |

TABLE 1-continued

| Progesterone Derivative or Peptide Analogue (see key) | Immunoreactivity | | Enzyme Inhibition Data | | |
|---|---|---|---|---|---|
| | Monoclonal 11P12 | Polyclonal | Enzyme | pH | Ki (μm) |
| | | 42.1% (HPS 53IIb) | | | |

KEY FOR TABLE 1

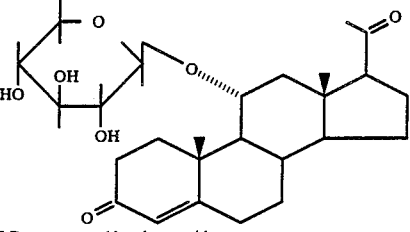

I Progesterone-11α-glucuronide

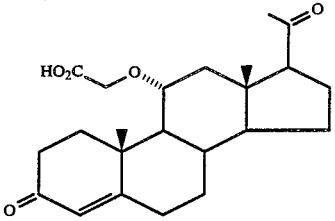

II Progesterone-11α-carboxymethylether
III His—leu—ser—phe—stat—ala—ile—pro—pro—lys—lys
IV Ac—his—leu—ser—stu—ala—ile—pro—pro—lys—lys

V

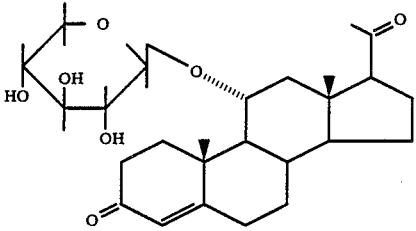

PSP1

VI

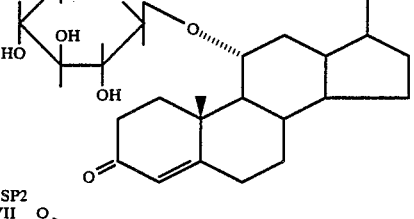

PSP2

VII

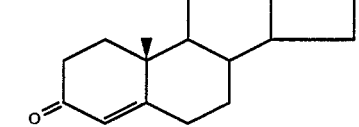

4. Testing of Progesterone-inhibitor conjugates for inhibition of chymosin milk-clotting activity and for modulation of their inhibition of chymosin milk-clotting activity by reaction with progesterone antibody Milk-clotting assays were carried out in the wells of microtiter plates. In each assay, after a suitable reaction time, the microtiter plate was inverted. Where clotting occurred, the clots remained in the wells of the plate, and where there was no clotting, the contents of the wells were decanted.

The general assay procedure was as follows:

20 μl of assay buffer containing 0.2% bovine serum albumin was pipetted into the wells of a microtiter plate. This was followed by 25 μl of assay buffer alone, or assay buffer containing the desired concentration of progesterone-inhibitor conjugate followed by 25 μl of assay buffer alone, or assay buffer containing the desired concentration of progesterone antibody. Then 30 μl of assay buffer containing the desired concentration of chymosin was added. This was followed by 100 μl of a milk substrate solution. The microtiter plate containing the assay mixture was placed in an incubator at 37° C. for 1 hour. At the end of this time the plate was inverted over a sink and tapped very lightly a few times, and then placed inverted on some tissue paper. The presence of clots was readily observed and either scored on a microtiter plate diagram or alternatively the inverted plate was photocopied against a dark background.

In order to demonstrate that an inhibition of chymosin milk-clotting activity by a progesterone-inhibitor conjugate could be modulated by immunoreaction of an antibody with a progesterone-inhibitor conjugate, a series of dilutions of chymosin were used together with a fixed amount of progesterone-inhibitor conjugate (sufficient to provide a noticeable inhibition of enzyme activity), a series of dilutions of progesterone antibody and a milk substrate in the previously described assay format.

Dilutions of chymosin in assay buffer were prepared at 1/1000, 1/1100, 1/1210, 1/1331, 1/1464, 1/1611, 1/1772, 1/1949. 30 μl of each diluted enzyme solution was used in each microtiter well. A solution of the progesterone-inhibitor designated P4SP2, at a concentration of 40 pmol/ml was prepared; 25 μl (1 pmol) being used in each microtiter well. Dilutions of sheep polyclonal antiserum HPS 53-IIb (supplied by Guildhay Antisera) were prepared at 1/50, 1/100 and 1/200; 25 ul of each dilution being used in each microtiter well.

Figure 2:
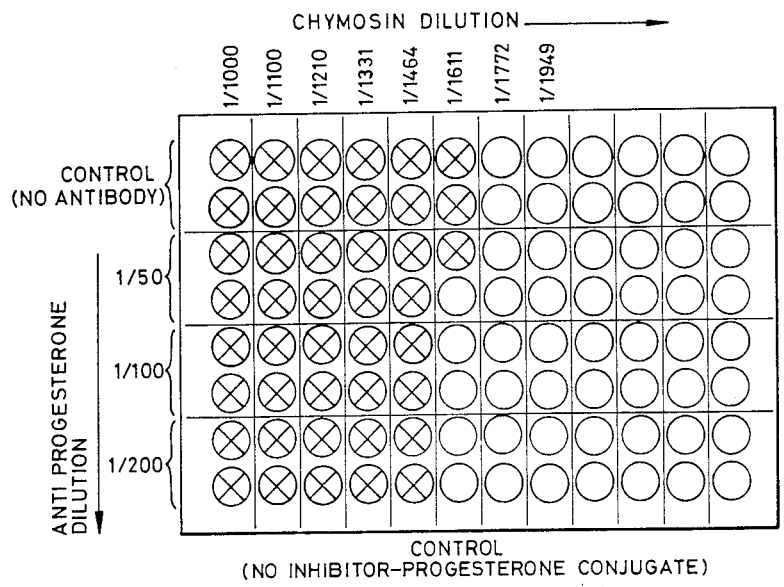
FIG. 2 shows the results of a "checkerboard" titration as in FIG. 1 without chymosin inhibitor-progesterone conjugate molecule.

The protocol followed was as described above. The results of the experiment are shown in FIGS. 1 and 2. FIG. 1 shows that inhibition of the milk clotting activity of chymosin, effected by the progesterone-inhibitor conjugate P4SP2, can be modulated by the addition of antibody. FIG. 2 shows the result of a control experiment in which no progesterone-inhibitor conjugate is present.

5. Immunoassay System for Detecting Steroid in Milk

The results of the experiment described above were used to select an antibody concentration at which modulation of the inhibition of chymosin milk clotting activity was possible. A further experiment was then conducted to investigate the effect of free steroid on the modulation of inhibitor activity by antibody.

Figure 3:
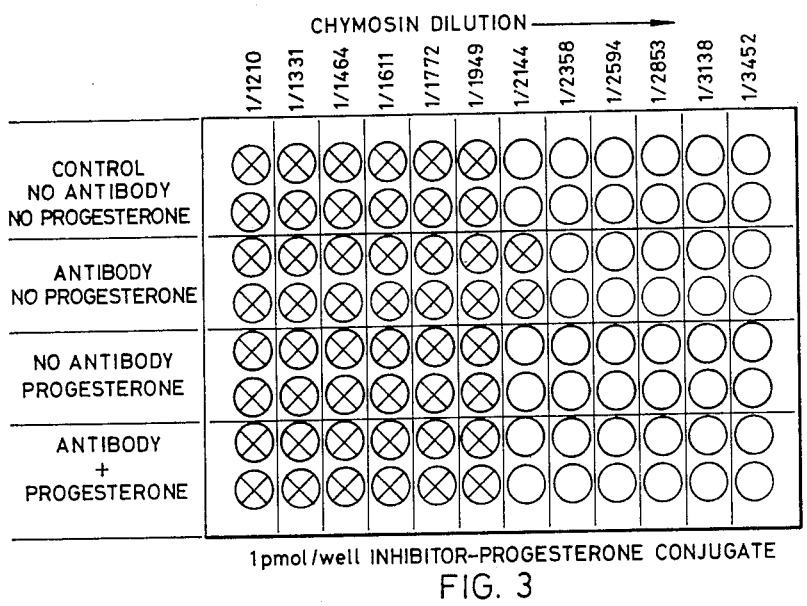
FIG. 3 shows the results of a titration on a microtiter plate indicating the effect upon milk samples of various dilutions of chymosin in the presence of anti-progesterone or progesterone or a combination of both, all wells having added chymosin inhibitor-progesterone conjugate molecule.
Figure 4:
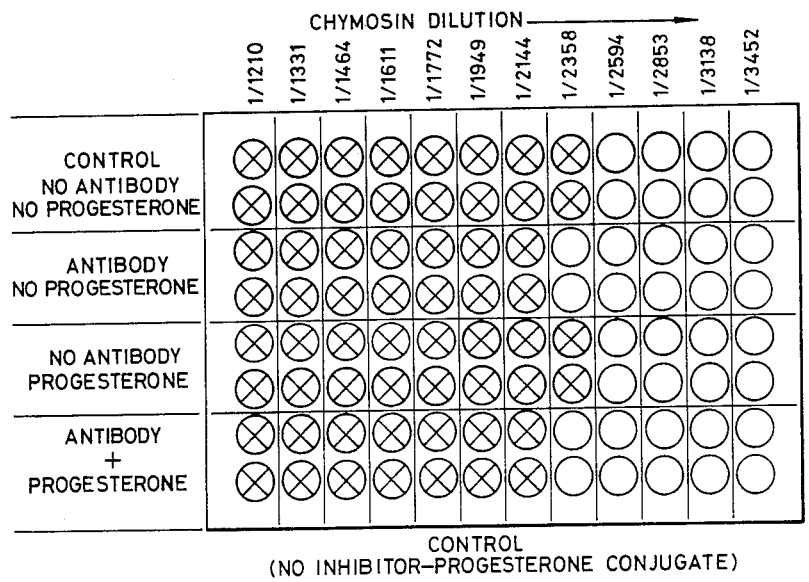
FIG. 4 shows the results of a titration on a microtiter plate as in FIG. 3 without chymosin inhibitor-progesterone conjugate molecule.

A 1/50 dilution of antibody to progesterone (HPS53 IIb—Guildhay antisera) was used, together with a fixed concentration of progesterone-inhibitor conjugate P4SP2 (100 pmol/ml). The final concentration of conjugate was 1 pmol/well. Progesterone was dissolved in assay buffer at a concentration of 0.5 nmol/ml, to give a final concentration of 7.5 pmol/well. Incubation mixtures containing 0.571 ml of assay buffer containing 0.2% BSA, 0.714 ml of dilute antibody, 0.429 ml of progesterone in assay buffer and 0.286 ml of inhibitor conjugate were prepared. Control incubates were also prepared in which antibody, progesterone, or both were replaced by equivalent volumes of assay buffer. A similar series of incubation mixtures in which progesterone-inhibitor conjugate was replaced by assay buffer was also prepared. These mixtures were incubated at 4° C. for 2 hours. At the end of the incubation, 70 μl of incubate was transferred to each well in duplicate rows on the microtitre plate. Dilution of a 1 mg/ml solution of chymosin in assay buffer were prepared as follows: 1/1210 1/1331, 1/1464, 1/1611, 1/1772, 1/1949, 1/2144, 1/2358, 1/2594, 1/2835, 1/3138, 1/3452. 30 μl of each dilution was added to each well in a column of the microtitre plates. These dilutions gave a final concentration of 0.71, 0.64, 0.58, 0.53, 0.48, 0.44, 0.40, 0.36, 0.33, 0.30, 0.27 and 0.25 pmol/well. 100 ul of milk substrate was added to each well and the plates were incubated for one hour at 37° C. before checking for clotting. The results obtained are shown in FIG. 3. The results obtained with the control plate are shown in FIG. 4. In the absence of progesterone, antibody and progesterone-inhibitor conjugate, the limiting concentration of chymosin necessary for clotting is 0.36 pmol/well. In the presence of progesterone alone, the limiting concentration remains the same, while in the presence of antibody it is increased to 0.40 pmol/well. When 1 pmol/well of the inhibitor is present, clotting is inhibited so that 0.44 pmol/well of chymosin is required to give a visible clot. As observed in the earlier experiment, clotting is restored in the preseance of antibody. However in the presence of progesterone, antibody restoration of clotting activity was impaired.

BIBLIOGRAPHY

1. Evolution in the Structure and Function Carboxyl Proteases. Jordan Tang Mol. Cell. Biochem., 1979, 26(2) 93–109.
2. The inactivation of Pepsin by Diazoacetyl-norleucine Methyl Ester, T. G. Rajagopalan, W. H. Stein and S. Moore J. Bio. Chem 1966, 241, 4295–4297.
3. Acid Proteases, Structure, Function and Biology, Edited by Jordan Tang, Plenum Press, New York and London, 1977.
4. Proteinases and their inhibitors, Structure, Function and Applied Aspects. Proc. Intern. Symp. Portoroz, Yugoslavia, 1980. Published 1981, Perganon Press.
5 Effect of Pepstatin on Acid Proteases T. Aoyagi, S. Kunimoto, H. Morishina, T. Takeuchi and H. Urnezawa, J. Antibiot., 1971, 24(10), 687–694.
6. Synthesis of Analogues of the Carboxyl Protease inhibitor Pepstatin. Effect of Structure on Inhibition of Pepsin and Renin. D. H. Rich, E. T. O. Sun and E. Uln. J. Med. Chem. 1980, 23 27–33.
7. Mechanism of Inhibition of Pepsin by Pepstatin. Effect of Inhibitor structure on dissocition constant and Time-Dependent Inhibition. D. H. Rich and E. T. O. Sun, Biochm. Pharmacol., 1980, 29 2205–2212.
8. New Renin Inhibitors homologous with pepstatin. M. Eid., G. Evin, B. Castro, J. Menard and P. Corvol., Biochem J 1981, 197 465–471.
9 The active Site of Acid Proteinases. T. L. Blundell, H. B. Jones, C. Khan, G. Taylor, B. T. Sewell, L. H. Pearl and S. P. Wood. FEBS Proc, 1980, 60, 281–288.
10. Synthesis of a 3-oxo-4(s)-amino acid analog of pepstatin. A New Inhibitor of Carboxyl (acid) proteases. D. H. Rich, A. S. Boparai and M. S. Bernatowicz, Biochem. Biophys. Res. Commun. 1982, 104(3), 1127–1133.
11 Spin-labelled Pepstatin Binding to Pepsin. A study by Electron spin Resonance and Nuclear Magnetic Resonance. P. G. Schmidt, M. S. Bernatowicz and D. H. Rich Biochemistry, 1982, 21, 1830–1835.

12. Solid-phase synthesis of a soluble pepstatin derivative suitable for therapeutic use. B. M. Austen, T. F. Ford, D. A. W. Grant and J. Hermon-Taylor. *Bioscience Reports*, 1982, 2, 427–432.

13. Inhibition of Cathepsin D by synthetic Oligopeptides. T-Y. Lin and H. R. Williams, *J. Biol. Chem.*, 1979, 11875–11883.

We claim:

1. An enzyme inhibitor-labelled immunoassay for measuring the concentration of an antigenic analyte in a milk sample, the immunoassay involving
   (i) the milk sample,
   (ii) a conjugate molecule comprising a moiety having at least one antigenic determinant in common with the antigenic analyte, the moiety being bonded to an inhibitor capable of inhibiting the activity of an enzyme capable of clotting milk such that the activity of the inhibitor is reduced or eliminated by the immunochemical binding of an antibody to the moiety,
   (iii) an antibody capable of forming an immunochemical bond to the said moiety of the conjugate molecule and to the antigenic analyte and
   (iv) an enzyme capable of clotting milk, the assay comprising the steps of allowing a competitive reaction to take place between antigenic analyte in the milk sample, the conjugate molecule and the antibody and determining the activity upon the milk sample of the enzyme capable of clotting milk.

2. An enzyme inhibitor-labelled immunoassay according to claim 1 wherein the enzyme used in the immunoassay is chymosin.

3. An enzyme inhibitor-labelled immunoassay according to claim 1 wherein the antigenic analyte is a steroid selected from the group consisting of a progestogen, a progestogen metabolite, an oestrogen and an oestrogen metabolite.

4. An enzyme inhibitor labelled immunoassay according to claim 3 wherein the antigenic analyte is progesterone.

5. A method for detecting oestrus in a domestic milk-producing animal comprising using an enzyme inhibitor labelled immunoassay according to claim 4 to monitor the concentration of progesterone in the milk of the animal, oestrus being indicated by a concentration of progesterone below a predetermined concentration.

6. A method according to claim 5 wherein the domestic milk-producing animal is a cow.

7. A method for detecting pregnancy in a domestic milk-producing animal comprising using an enzyme inhibitor labelled immunoassay according to claim 4 to monitor the concentration of progesterone in the milk of the animal, pregnancy being indicated by the lack of a drop in the concentration of progesterone below a predetermined concentration at a time when oestrus would be expected.

8. A method according to claim 7 wherein the domestic milk-producing animal is a cow.

9. An enzyme inhibitor labelled immunoassay according to claim 3 wherein the antigenic analyte is oestrone sulphate.

10. A method for detecting pregnancy in a milk-producing domestic animal comprising using an enzyme inhibitor labelled immunoassay according to claim 9 to monitor the concentration of oestrone sulphate in the milk of the animal, pregnancy being indicated by a concentration of oestrone sulphate above a predetermined concentration.

11. A method according to claim 10 wherein the domestic milk-producing animal is a cow.

12. An enzyme inhibitor-labelled immunoassay according to claim 1 wherein the antigenic analyte is an aflatoxin metabolite.

13. A method for monitoring aflatoxin in the milk of a milk-producing domestic animal comprising using an enzyme inhibitor labelled immunoassay according to claim 12 to measure the concentration of an aflatoxin metabolite in the milk of the animal.

14. A method according to claim 13 wherein the domestic milk-producing animal is a cow.

15. An assay according to claim 12 or a method according to claim 13 wherein the aflatoxin metabolite is aflatoxin $M_1$.

16. A reagent kit for performing an enzyme inhibitor-labelled immunoassay for measuring the concentration of an antigenic analyte in a milk sample, the kit comprising:
   a conjugate molecule,
   an antibody, and
   an enzyme capable of clotting milk,
   wherein the said conjugate molecule comprises a moiety having at least one antigenic determinant in common with the said antigenic analyte, the moiety being bonded to an inhibitor capable of inhibiting the activity of the said enzyme,
   wherein the antibody is capable of competitively forming an immunochemical bond to the said moiety of the conjugate molecule and to the antigenic analyte, and
   wherein the activity of the inhibitor is modulated by the formation of an immunochemical bond between the said moiety of the conjugate molecule and the antibody.

17. A reagent kit according to claim 16 wherein the kit comprises:
   a first container containing the conjugate molecule,
   a second container containing the antibody, and
   a third container containing the enzyme.

18. A reagent kit according to claim 16 wherein the kit comprises:
   a first container containing the conjugate molecule and the enzyme, and
   a second container containing the antibody.

* * * * *